(12) United States Patent
Acton et al.

(10) Patent No.: US 6,361,934 B1
(45) Date of Patent: Mar. 26, 2002

(54) METHOD AND APPARATUS FOR CRYOPRESERVATION

(76) Inventors: Elizabeth Acton, New Hall, Huntingdon Road, Cambridge CB3 0DF; George John Morris, Thatched Cottage, Caxton Road, Bourn, Cambridge CB5 7SX, both of (GB)

( * ) Notice: Subject to any disclaimer, the term of this patent is extended or adjusted under 35 U.S.C. 154(b) by 0 days.

(21) Appl. No.: 09/529,667

(22) PCT Filed: Oct. 22, 1998

(86) PCT No.: PCT/GB98/03160

§ 371 Date: Jun. 23, 2000

§ 102(e) Date: Jun. 23, 2000

(87) PCT Pub. No.: WO99/20104

PCT Pub. Date: Apr. 29, 1999

(30) Foreign Application Priority Data

Oct. 22, 1998 (GB) .............................................. 9722156

(51) Int. Cl.⁷ ................................................. A01N 1/02
(52) U.S. Cl. .................. 435/2; 128/898; 128/DIG. 27; 424/561; 435/3; 436/8
(58) Field of Search ............................ 62/3, 62, 68, 67, 62/78, 328, 381, 48.11, 448; 424/93, 72, 93.73, 533, 56; 435/1.1, 1.2, 1.3, 2, 13.2, 21.9, 260; 436/8, 10, 18; 128/898, DIG. 27

(56) References Cited

U.S. PATENT DOCUMENTS 4,474,015 A 10/1984 Christmas et al.
5,045,446 A * 9/1991 Goodrich, Jr. et al. .......... 435/2
5,364,756 A * 11/1994 Livesey et al. ................. 435/2
5,629,145 A * 5/1997 Meryman .................... 435/1.3

FOREIGN PATENT DOCUMENTS

| DE | 2929278 | 1/1981 |
| DE | 3125345 | 1/1983 |
| WO | 9101635 | 2/1991 |
| WO | 9602801 | 2/1996 |
| WO | 9823907 | 6/1998 |

OTHER PUBLICATIONS

Chemical Abstracts, vol. 104, No. 3 Jan. 20, 1986.
Biofizica vol. 30, No. 6, 1985, pp. 1042–1045.

* cited by examiner

Primary Examiner—Leon B. Lankford, Jr.
Assistant Examiner—Kailash C. Srivastava
(74) Attorney, Agent, or Firm—Stevens, Davis, Miller & Mosher, L.L.P.

(57) ABSTRACT

A method of cryopreserving biological material, which method comprises providing a sample of the biological material, where a liquid phase of the sample includes at least one solute; lowering the temperature of the sample to a nucleating point at which ice nucleation can occur in the sample; effecting ice nucleation in the sample; and lowering the sample temperature from the nucleating point to the solidification point thereof, characterized in that the temperature lowering from the nucleating point to the solidification point is non linear, whereby the rate of change of solute concentration in the liquid phase decreases for more than 80% of the time taken to lower the temperature from the nucleating point to the solidification point.

11 Claims, 4 Drawing Sheets

METHOD AND APPARATUS FOR CRYOPRESERVATION

The present invention relates to a method and apparatus for cryopreserving biological material including, for example, cell suspensions, such as embryos, gametes, (spermatozoa, oocytes) cell lines, bone marrow, blood stem cells and the like; solutions of proteins and/or other biologically active substances; and perfused tissues and organs, either engineered or obtained from a natural source.

Cryopreservation is a process where samples such as biological materials are stored at low temperatures. Cryopreservation of biological material substantially as described above is generally effected by freezing in appropriate retaining means, such as flexible bags, glass or plastic ampoules, or plastic tubes (usually referred to as "straws" in the field of cryopreservation) of the type suitable for long term storage at the low temperatures employed.

Although cryopreservation has been widely employed for a range of biological materials, there are certain materials for which it is not suitable. For example, with certain materials, cellular injury can occur on thawing. Furthermore, cryopreservation is not applicable for cell types where recovery on thawing may either be low or very variable, or even non-existent. For example, recovery on thawing of sub-fertile human spermatozoa, human testicular spermatozoa, pig spermatozoa and the like is generally low or variable, and in other cases such as mammalian oocytes, fish eggs, fish embryos, tissues, organs or the like, survival is non-existent.

Furthermore, on thawing cryopreserved material, cell survival can be dependent on the conditions and techniques employed, such as appropriate nucleation techniques, addition of suitable cryoprotective additives and also the control of the cooling rate. Nucleation, for example, is known to be a problem when not externally controlled in cryopreservation techniques, and occurs at a wide range of temperatures below the melting point of individual materials. While some materials nucleate at or just below the melting point, others may not nucleate until the temperature has reached up to 20° C. below the melting point, for example, with cell suspensions contained in straws or ampoules the range of temperature is particularly wide, both because the volume of the suspensions, and hence the number of available heteronuclei, is small and also because the containers are generally sealed before freezing, thus removing the possibility of seeding by airborne ice nuclei in the freezer. Nucleation at temperatures significantly away from melting points of materials requiring cryopreservation has resulted in transient temperature changes and cell death even when cooling rates have apparently been optimised for survival (Whittingham D. G., In The Freezing Of Mammalian Embryos, Ciba Foundation Symposium 52, pp 98–102, 1977).

In order to nucleate biological materials in a reproducible manner, it is common practice firstly to cool the materials to a temperature below the melting point thereof, then after a short period of thermal equilibration, to nucleate ice in the supercooled material. Nucleation can be achieved by any of the following techniques—application of cold forceps to the outside of the material, by cold wires, by devices employing "reverse Peltier effects" or by the application of physical disturbances. An alternative method of ensuring nucleation near to the melting point is to incorporate an ice nucleating agent into the biological suspension before temperature reduction. Examples of ice nucleating agents include the so called ice nucleating bacteria for example Pseudomonas syringae, the active proteins from ice nucleating bacteria and organic compounds such as cholesterol. Following nucleation and initial crystal growth, cooling of the materials is then resumed.

However, monitoring the success of the nucleation procedure and also subsequent crystal growth has proved to be a problem. In conventional controlled rate freezing equipment, it is not possible to monitor subsequent crystal growth following nucleation without removing the straws from the equipment for visual inspection. A high risk of melting is associated with such removal. Furthermore, at present no method is available in such equipment to monitor, in a non-invasive manner, the success of the nucleation procedure.

Problems have also been encountered as a result of the techniques employed to lower the temperature following nucleation. It is common practice that during cryopreservation, biological materials are cooled with, as far as possible, a linear reduction in temperature with time. Cryopreservation equipment is generally designed to control the material environment in a linear manner, and depending on the heat transfer characteristics of the equipment, the materials cool in a more or less linear manner. Whilst this approach is convenient for simple design of equipment and has produced acceptable results with a range of cell types, it has proved unsatisfactory with a number of cellular materials.

WO96/02801 discusses the importance of employing a linear cooling rate over the entire cooling phase employed in cryopreservation, and is concerned with the provision of a cooling assembly capable of obtaining a substantially linear and reproducible rate of cooling samples.

WO96/24018 is concerned with the cryopreservation of mammalian tissue, or living cultured equivalents made by in vitro technology. The temperature control employs linear temperature lowering, but different rates of linear temperature lowering are respectively employed in different stages of the cryopreservation process. More particularly, the temperature is initially lowered at a rate of −10.0° C./minute to the solid-liquid phase equilibrium temperature range for an employed cryoprotectant, and following propagation of ice seed crystals throughout the cryoprotectant cooling is resumed at a rate of between −0.02 to about −0.3° C./minute.

U.S. Pat. No. 4,799,358 describes freezing of biological material, and also employs linear temperature lowering but with different rates of linear temperature lowering being respectively employed in different stages of the freezing process. For example, the temperature is typically initially lowered at a rate of −0.5° C./minute between +20° C. and −7° C. and then −0.3° C./minute between −7° C. and −35° C.

The use of non-linear cooling rates has also been discussed in the prior art. WO91/01635 is concerned with a cooling process and apparatus where the material being frozen is subjected to a greater rate of heat extraction when the latent heat is being given up during nucleation, than when the material is cooled further. WO91/01635 indicates that the heat extraction rates may be non-linear, but does not provide clear guidance as to the parameters of non-linear heat extraction employed.

We have now devised a method and apparatus for cryopreserving biological material, which method and apparatus reduce or alleviate the problems associated with the prior art. In particular, we have devised a method and apparatus to reduce or overcome the problems associated with cellular freezing injury.

According to the present invention, there is provided a method of cryopreserving biological material, which method comprises: providing a sample of the biological material, where a liquid phase of the sample includes at least one solute; lowering the temperature of the sample to a nucleating point at which ice nucleation can occur in the sample; effecting ice nucleation in the sample; and lowering the temperature of the sample from the nucleating point to the solidification point thereof, characterised in that the temperature lowering from the nucleating point to the solidification point is non-linear, whereby the rate of change of solute concentration in the liquid phase decreases for more than 80% of the time taken to lower the temperature from the nucleating point to the solidification point.

Preferably, in the method of the invention the liquid phase is aqueous and, preferably, the biological sample is suspended or dissolved therein.

The term "solidification point" as used herein denotes the temperature at which substantially all the liquid phase of the sample solidifies, or vitrifies. This temperature can be determined from a phase diagram or may be measured by differential scanning calorimetry. For simple solutions, the solidification point is the eutectic temperature.

Preferably, the method of the present invention comprises determining the melting point of the sample. Suitably, the melting point can be determined based on the osmolality of the liquid phase, and a method according to the present invention aptly further comprises determining the osmolality of the liquid phase. Osmolality can be determined by any convenient technique known in the art, such as solidification point osmometry, or may be calculated from the composition of the liquid phase. The equilibrium phase diagram during solidification or freezing can then be constructed by an appropriate method, including experimental measurement, by reference to standard text (for example the CRH Handbook of Chemistry and Physics) or scientific publication (for example Rasmussen & Mckenzie, Nature 220, 1315–1317, 1968, Shepard et al., Cryobiology 13, 9–23, 1976, Lane, Ind. Engr. Chem. 17, 924, 1925). For solutions with unpublished or incomplete phase diagrams, and for complex mixed solutions, the phase diagram may be approximated by any well defined system, for example glycerol and water (Lane, Ind. Engr. Chem. 17, 924, 1925).

The method according to the present invention preferably includes determining the nucleating point of the sample. Preferably, the nucleating point should be substantially close to the melting point. In a particularly preferred embodiment, the nucleating point should not be less than about 4° C. below the melting point. Even more preferably, the nucleating point should not be less than about 2° C. below the melting point. Ice nucleation can be achieved by employing any known prior art techniques substantially as herein before described.

In a first embodiment of the present invention, the method can further comprise a step of thermal re-equilibration following ice nucleation. In a second embodiment of the present invention, for example where large sample volumes (such as cell suspensions, or perfused tissues or organs) are being cryopreserved in flexible bags, substantially no re-equilibration is carried out.

Substantially as herein before described, the temperature lowering from the nucleating point to the solidification point is non-linear, so that the rate of change of solute concentration in the liquid phase decreases for more than 80% of the time taken to lower the temperature from the nucleating point to the solidification point. It will be appreciated, however, that any particular such non-linear thermal profile will be substantially dependent on the biological material being cryopreserved, the concentration thereof, solute concentration or concentrations and also the presence of any other additives in the sample.

It is further particularly preferred that temperature lowering from the nucleating point to the solidification point is non-linear so that the rate of change of solute concentration in the liquid phase decreases for more than 90% of the time taken to lower the temperature from the nucleating point to the solidification point. Advantageously, the change in solute concentration during the time taken to lower the temperature from the nucleating point to the solidification point is closely approximated by $$A=26.9+30.6\ tan^{-1}\{(t+t_0-0.385)/1.17\}$$

where t is the time at which the temperature is begun to be lowered from the nucleating point, and $t_0$ is determined from the concentration $A_0$ according to the equation $$t_0=0.385+1.17 tan\{0.0327(A_0-26.9)\}.$$

Typically, the sample employed in a method according to the present invention contains one or more cryoprotectants. A suitable cryoprotectant can include a solution of glycerol, fructose and sodium citrate.

The method according to the present invention preferably further involves determining the time to be taken for the non-linear temperature lowering from the nucleating point to the solidification point. The time elapsed from the nucleation point to the solidification point can be dependent on a number of factors, such as the biological material being cryopreserved, and suitably also the cryoprotectant employed, and can be determined in a number of ways.

For example, the elapsed time can suitably substantially correspond to the time that would be taken from the nucleating point to the solidification point where the optimal linear rate of cooling was employed for a selected biological material. The optimal linear rate of cooling for mammalian spermatozoa is −10° C. and −0.3° C. for mammalian embryos. This optimum linear rate of cooling may be estimated from a knowledge of the basic biophysical parameters that determine osmotic behaviour during solidification.

Particularly for cell suspensions, perfused tissues or organs, however, the elapsed time during the non-linear cooling employed in the present invention can be determined by modelling the osmotic behaviour during solidification. Accordingly, the elapsed time may be determined by selecting the shortest time that achieves sufficient water loss so as to substantially avoid any intracellular ice formation in the cells of the biological material, during any of the temperature lowering steps employed in the present invention.

Biological material employed in a method according to the present invention suitably comprises cell suspensions, such as embryos, gametes (spermatozoa, oocytes), cell lines, bone marrow, blood stem cells or the like; solutions of proteins and/or other biologically active substances; and perfused tissues and organs, either engineered or obtained from a natural source.

There is further provided-by the present invention biological material substantially as herein before described cryopreserved by a method substantially as herein before described.

There is still further provided by the present invention apparatus for cryopreserving a biological material, which apparatus comprises means for receiving one or more samples of the biological material, where a liquid phase of the sample or samples includes at least one solute; means for lowering the temperature of the sample or samples to a nucleating point thereof at which ice nucleation can occur in the sample or samples; means for effecting ice nucleation in the sample or samples; and means for lowering the temperature of the sample or samples from the nucleating point to a solidification point thereof, characterised in that the temperature lowering means effect non-linear temperature lowering from the nucleating point to the solidification point, whereby the rate of change of solute concentration in the liquid phase decreases for more than 80% of the time taken to lower the temperature from the nucleating point to the solidification point.

Suitably the receiving means of apparatus according to the present invention are dimensioned so as to be suitable for receiving sample retaining means generally employed in cryopreservation, such as plastic tubes (commonly known in the field of cryopreserving as "straws") for the biological sample or samples. Appropriately, the receiving means can comprise a grooved (typically machined) holder for the retaining means such as straws, and can generally comprise a suitable thermally conductive material. Generally, the grooved holder is substantially horizontally arranged for receiving the straws. Alternatively, where the retaining means comprise plastic ampoules or glass vials, the holder can comprise substantially vertically arranged apertures for receiving these retaining means. Where plastic ampoules are employed as the retaining means, it is generally preferable to employ transparent lids for the ampoules to facilitate nucleation detection substantially as herein after described.

The apparatus appropriately further comprises means for illuminating one or more biological samples arranged therein. The illuminating means may simply comprise a light source remotely arrangeable relative to the receiving means to illuminate straws or the like. Alternatively, the illuminating means may comprise transparent plug means for axially illuminating samples being cryopreserved according to the present invention. In the latter case, the presence of ice can be indicated by sideways scattering form a resulting axial light beam.

It may be desirable for the receiving means to be adapted (for example by surface colour and/or finish modification) to enhance detection of optical contrast occurring following nucleation. Suitably, an indicator may be included in a sample being cryopreserved according to the present invention so that changes in selected physical properties of the sample can be detected following ice formation. For example, a pH indicator capable of providing a colorimetric indication of pH change may be employed.

It is further preferred that apparatus according to the present invention further comprises means for viewing a sample or samples arranged therein. For example, the receiving means may suitably be arrangeable within a chamber of which at least one wall portion comprises a transparent material so as to allow viewing of a sample or samples arranged in the chamber. The wall portion may comprise an insulating material, such as Perspex, and may further be provided with an insulating cover that may be removed to allow inspection of a sample or samples being cryopreserved according to the present invention. In this way, if nucleation has been unsuccessful this can be detected and substantially rectified. For example, nucleation may be repeated for a sample or samples that have been detected not to have previously undergone nucleation, and this will not be detrimental for samples in the apparatus according to the present invention that have previously undergone successful nucleation.

This aspect of the present invention is particularly advantageous, as successful detection of ice nucleation can be an important parameter in achieving successful cryopreservation.

The temperature lowering means employed in apparatus according to the present invention may comprise a feedback loop incorporating means of temperature measurement, a controller and a thin film heater.

The present invention will now be further illustrated by the following figures and example, which do not limit the scope of the invention in any way.

Figure 1:
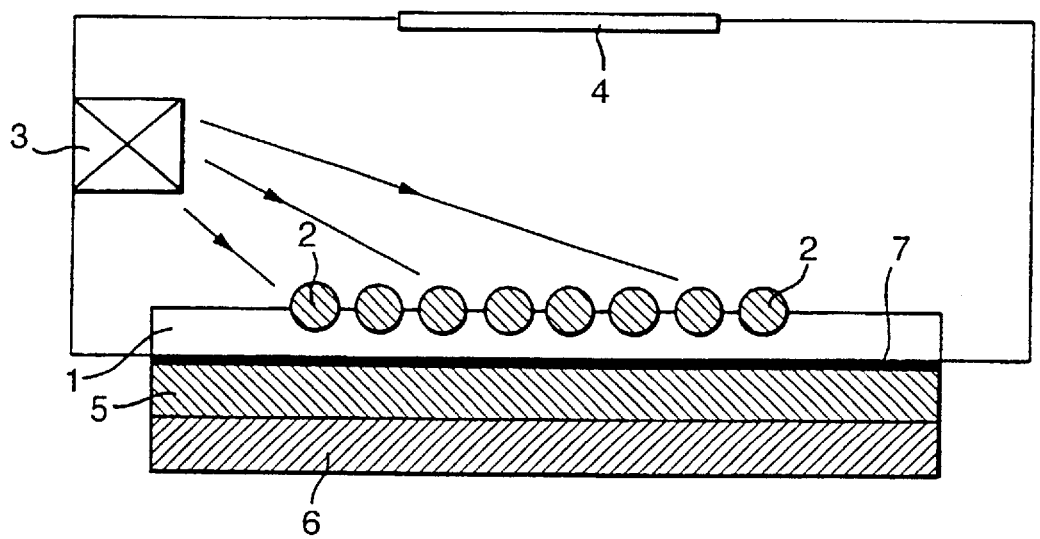
FIG. 1 is a side view of a holder (1) for receiving horizontally arranged straws (2) containing suspensions to be cryopreserved, where the suspensions are illuminated by a remote light source (3).
Figure 2:
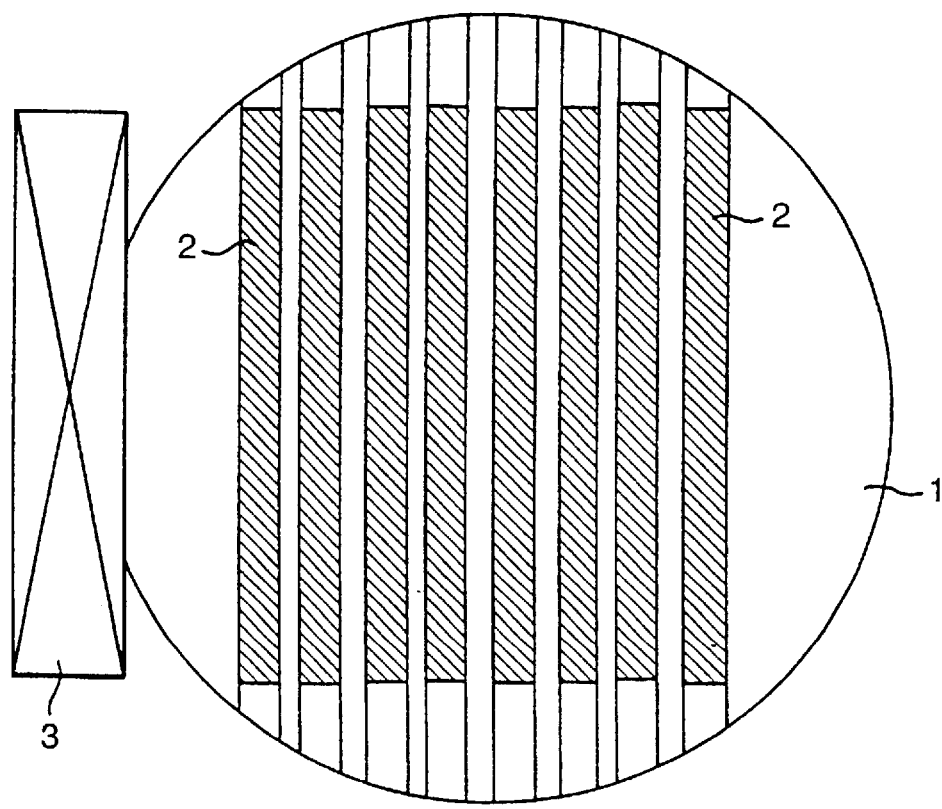
FIG. 2 is a plan view of holder (1) shown in FIG. 1.

FIGS. 1 and 2 show suspension holder (1) in which suspensions are illuminated by a light source (3). Light source (3) is positioned so as to enable ice within straws (2) to be visualised through a viewing window (4). Heat is continually extracted from holder (1) through an insulating plate (5) to a cold heat sink (6). The temperature of holder (1) is measured by any suitable technique, such as a thermocouple (not shown) and a thin film heater (7) is then used to control the temperature of holder (1) as required. Temperature control during solidification is achieved using any suitable controller that may be programmed to achieve non-linear rates of temperature change.

Figure 3:
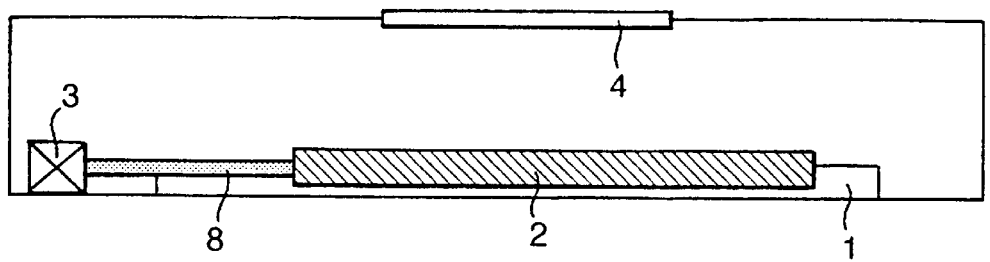
FIG. 3 is a side view of a holder (1) for receiving horizontally arranged straws (2) containing suspensions to be cryopreserved, where the suspensions are illuminated through light guides (8).
Figure 4:
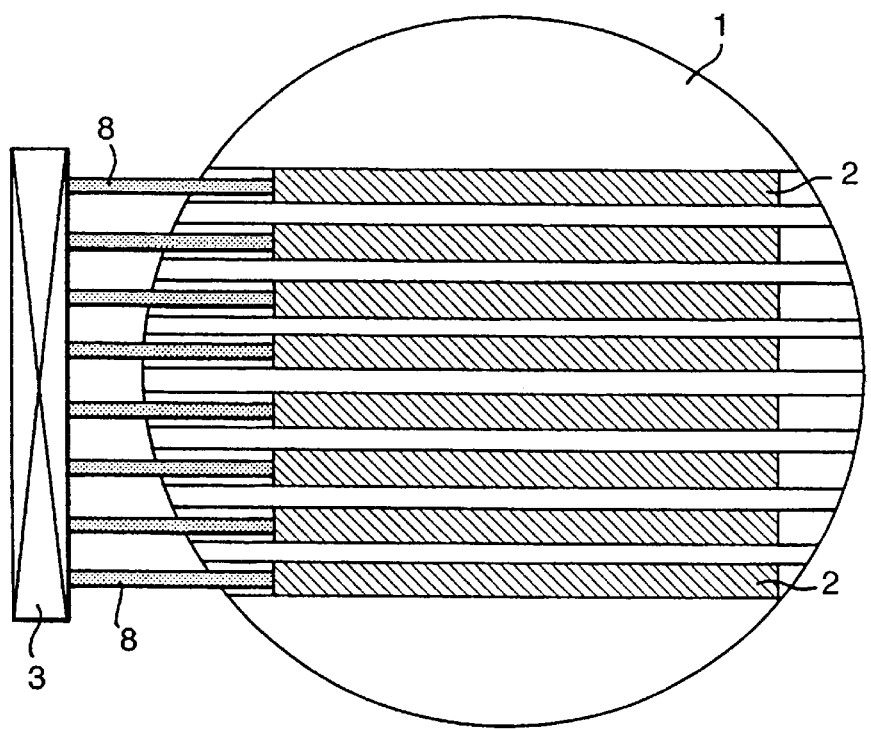
FIG. 4 is a plan view of holder (1) shown in FIG. 3.

FIGS. 3 and 4 show holder (1) in which straws (2) are illuminated axially through light guides (8) at the end of straws (2). Light source (3) provides light to guide 8.

Figure 5:
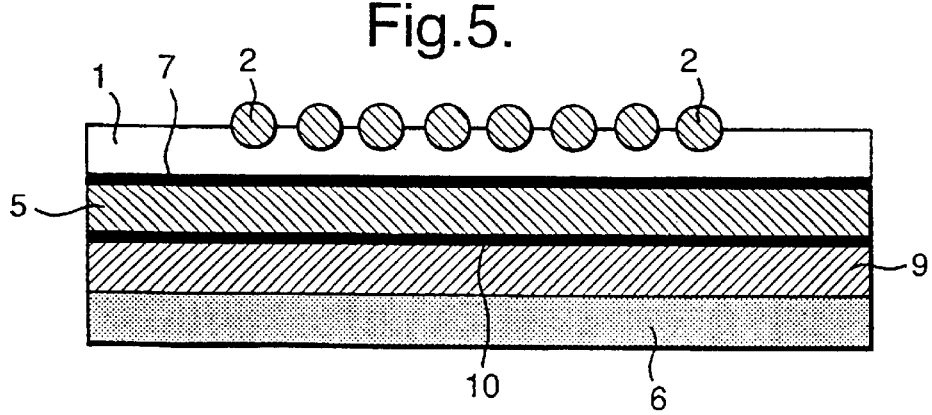
FIG. 5 is a side view of a passive cooler for use in method and apparatus according to the present invention.

FIG. 5 shows a passive cooler suitable for use in method and apparatus according to the present invention. The temperature of holder (1) up to ice nucleation of the suspensions is controlled by upper thin-film heater (7) backing off the cooling to heat sink (6). Two insulated plates (5) and (9) are used, with a second thin-film heater (10) therebetween. Heater (10) is used to maintain the temperature at the bottom of upper insulated plate (5) at a predetermined temperature ($T_1$). After nucleation, the upper heater (7) is switched off and holder (1) then cools passively to temperature $T_1$. After a predetermined time second heater (10) is switched off and holder (1) cools to the temperature of cold heat sink (6).

EXAMPLE 1

Cryopreservation of Human Spermatozoa

Figure 6:
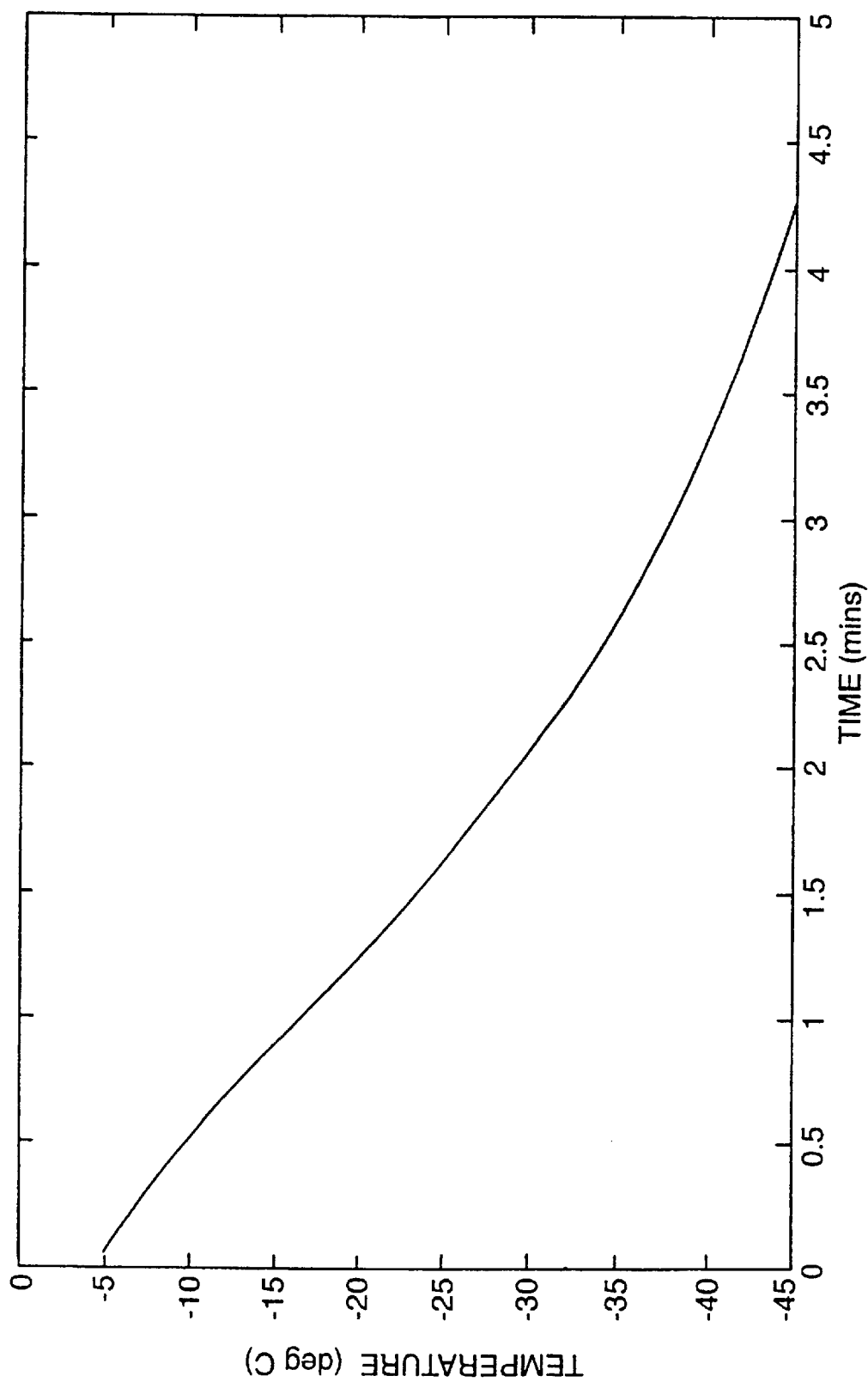
Figure 7:
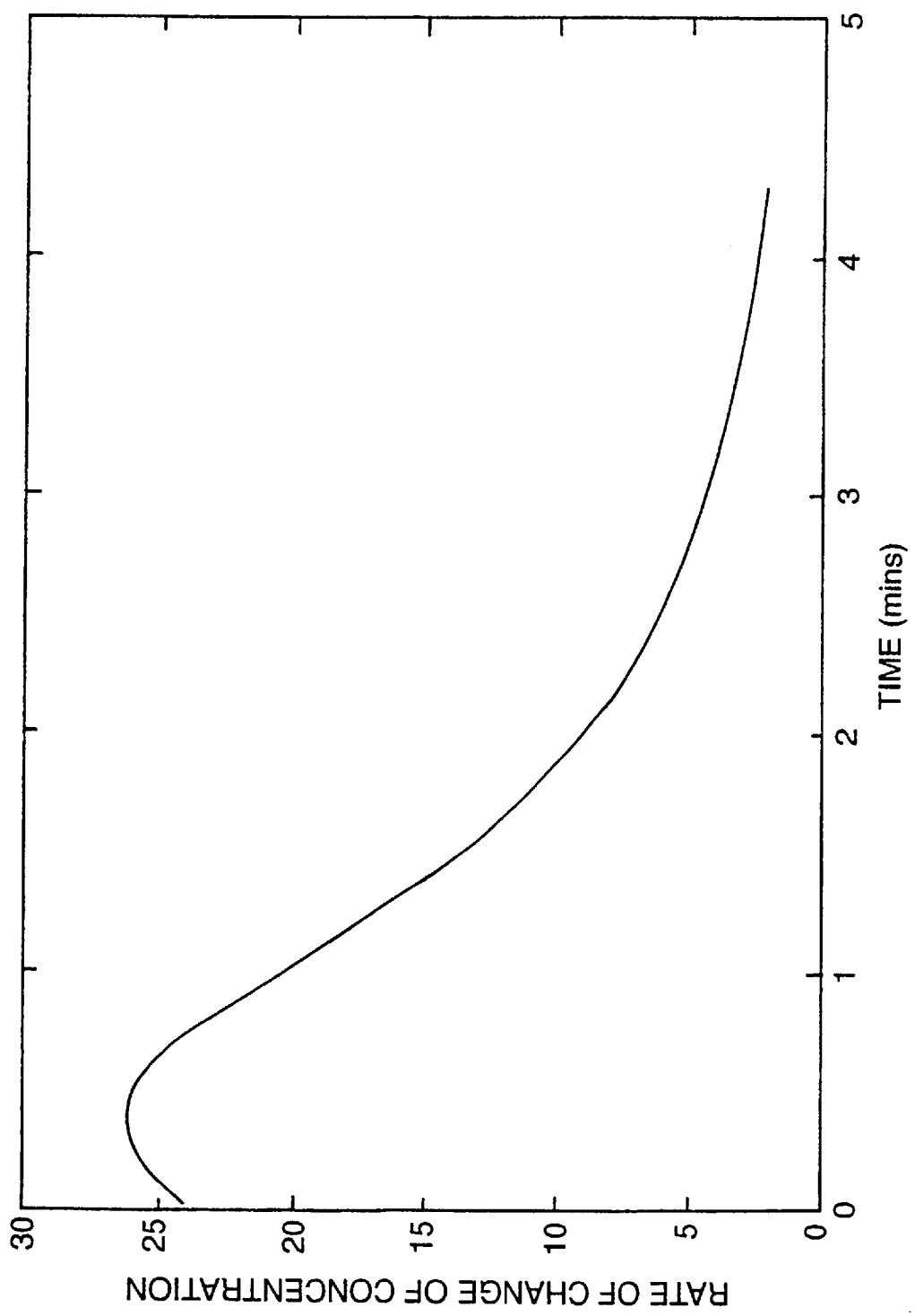

Normal human sperm was diluted into a cryoprotectant solution containing glycerol, fructose and sodium citrate prior to freezing. The osmolality of the cell suspension was measured to be 1430 mOsm/Kg by freezing point osmometry, equivalent to an aqueous glycerol solution of 13.5 w/v. The temperature-time curve to achieve a change in solute concentration of the unfrozen fraction that was decreasing for >90% of the elapsed time was then determined and is shown in FIG. 6 together with the calculated time-concentration curve shown in FIG. 7. The elapsed time from −5° C. (the nucleation temperature) to −45° C. (the eutectic temperature for glycerol/water was 4 minutes.

Straws (0.25 ml IMV, L'Aigle France) were filled with the cell suspension and sealed with PVA powder. The straws were placed in apparatus of the type shown in FIG. 1 and cooled from 20° C. to −5° C. at a rate of 2° C./min. At −5° C. the straws were nucleated within the equipment by touching the straw at the free surface of the liquid column with a nucleating tool that had been cooled by immersion into liquid nitrogen. Confirmation that ice had formed in all straws was achieved by direct observation of illuminated straws on the cooling plate. The temperature of the straws was then reduced to −45° C. following the temperature time curve shown in FIG. 6. Straws were then cooled to −100° C. at a rate of 10° C./min and then transferred to liquid nitrogen for storing. When required straws were then thawed at room temperature and the motility assessed.

With all sperm samples examined sperm frozen by a method according to the present invention had a significantly higher recovery than sperm frozen by a passive vapour phase cooling protocol or by linear cooling at a rate of −10° C./min within a conventional controlled rate freezer. For example, with sperm from one ejaculate, vapour phase cooling yielded 60% motile sperm on thawing whilst linear cooling within a controlled rate freezer yielded 66%, samples frozen by a method according to the present invention had a recovery on thawing of 88%.

What is claimed is:

1. A method of cryopreserving biological material, which method comprises:

providing a sample of the biological material, where a liquid phase of the sample comprises at least one solute;

lowering the temperature of the sample to a nucleating point at which ice nucleation can occur in the sample;

effecting ice nucleation in the sample; and lowering the temperature of the sample non-linearly with respect to time from the nucleating point to its solidification point, wherein said non-linear temperature lowering is such that the rate of change of solute concentration in the liquid phase decreases for more than 80% of the time taken to lower the temperature from the nucleating point to the solidification point.

2. A method according to claim 1, which further comprises determining the melting point of the sample.

3. A method according to claim 1, which further comprises determining the osmolality of the liquid phase.

4. A method according to claim 1, which further comprises determining the nucleating point of the sample.

5. A method according to claim 1, wherein the nucleating point should not be less than about 4° C. below the melting point.

6. A method according to claim 5, wherein the nucleating point should not be less than about 2° C. below the melting point.

7. A method according to claim 1, wherein the method further comprises the step of thermal re-equilibration following nucleation.

8. A method according to claim 1, wherein lowering the temperature from the nucleating point to the solidification point is non-linear so that the rate of change of solute concentration in the liquid phase decreases for more than 90% of the time taken to lower the temperature from the nucleating point to the solidification point.

9. A method according to claim 1, wherein the change in solute concentration during the time taken to lower the temperature from the nucleating point to the solidification point is closely approximated by $$A=26.9+30.6 \tan^{-1} \{(t+t_0-0.385)/1.17\}$$

where t is the time at which the temperature is begun to be lowered from the nucleating point, and $t_0$ is determined from the concentration $A_0$ according to the equation $$t_0=0.385+1.17 \tan \{0.0327(A_0-26.9)\}.$$

10. A method according to claim 1, wherein the sample contains a cryoprotectant.

11. A method according to claim 1, wherein the sample contains an ice nucleating agent.

* * * * *